United States Patent
Zhang et al.

(10) Patent No.: US 11,053,449 B2
(45) Date of Patent: Jul. 6, 2021

(54) THIOETHER-CONTAINING PHENOLIC COMPOUNDS

(71) Applicant: The Lubrizol Corporation, Wickliffe, OH (US)

(72) Inventors: Yanshi Zhang, Solon, OH (US); Jason J. Hanthorn, Eastlake, OH (US)

(73) Assignee: The Lubrizol Corporation, Wickliffe, OH (US)

( * ) Notice: Subject to any disclaimer, the term of this patent is extended or adjusted under 35 U.S.C. 154(b) by 269 days.

(21) Appl. No.: 15/774,313

(22) PCT Filed: Nov. 8, 2016

(86) PCT No.: PCT/US2016/060891
§ 371 (c)(1),
(2) Date: May 8, 2018

(87) PCT Pub. No.: WO2017/083243
PCT Pub. Date: May 18, 2017

(65) Prior Publication Data
US 2020/0239805 A1 Jul. 30, 2020

Related U.S. Application Data

(60) Provisional application No. 62/253,821, filed on Nov. 11, 2015.

(51) Int. Cl.
| | | |
|---|---|---|
| *C10M 135/26* | (2006.01) | |
| *C07C 323/12* | (2006.01) | |
| *C10N 30/04* | (2006.01) | |
| *C10N 40/25* | (2006.01) | |

(52) U.S. Cl.
CPC .......... *C10M 135/26* (2013.01); *C07C 323/12* (2013.01); *C10M 2219/085* (2013.01); *C10N 2030/04* (2013.01); *C10N 2040/25* (2013.01)

(58) Field of Classification Search
CPC .......... C10M 135/26; C10M 2219/085; C10N 2030/12; C10N 2040/25
USPC ....................................................... 508/501
See application file for complete search history.

(56) References Cited

U.S. PATENT DOCUMENTS

| | | | | |
|---|---|---|---|---|
| 3,285,855 A | * | 11/1966 | Dexter | C08K 5/1345 508/476 |
| 3,457,286 A | * | 7/1969 | Dexter | C08K 5/17 554/63 |
| 3,810,869 A | * | 5/1974 | Zaweski | C07C 323/00 524/130 |
| 3,984,460 A | | 10/1976 | Spivack | |
| 4,532,286 A | * | 7/1985 | Rosenberger | C08K 5/37 508/501 |
| 4,889,883 A | * | 12/1989 | Rosenberg | C07C 323/00 524/289 |
| 4,954,275 A | * | 9/1990 | Rosenberger | C10M 135/26 508/501 |
| 5,658,866 A | * | 8/1997 | Yoshida | C10M 129/76 508/503 |
| 5,912,212 A | * | 6/1999 | Igarashi | C10M 141/10 508/275 |
| 6,750,184 B2 | * | 6/2004 | Ribeaud | C10M 141/10 508/375 |
| 2003/0148900 A1 | * | 8/2003 | Palazzotto | C10M 129/70 508/501 |

OTHER PUBLICATIONS

Chinese Office Action Issued by for Chinese Patent Application No. 201680072001.4, dated Dec. 18, 2020.

* cited by examiner

*Primary Examiner* — Ellen M Mcavoy
(74) *Attorney, Agent, or Firm* — Iken Sans; Teresan Gilbert

(57) ABSTRACT

Thioether-substituted phenols that are the reaction product of a thioether-substituted alcohol or thioether-substituted amine and a phenol with at least one pendant acyl group and have a ratio of sulfur groups to phenol groups of at least 1:1 and uses for thioether-substituted phenols. Methods of lubricating an internal combustion engine by contacting the internal combustion engine with a lubricating composition comprising a thioether-substituted phenol. Methods of reducing deposit formation and/or corrosion in an engine using a lubricating composition comprising a thioether-substituted phenol.

6 Claims, No Drawings

THIOETHER-CONTAINING PHENOLIC COMPOUNDS

CROSS REFERENCE TO RELATED APPLICATION

This application claims priority from PCT Application Serial No. PCT/US2016/060891 filed on Nov. 8, 2016, which claims the benefit of U.S. Provisional Application No. 62/253,821 filed on Nov. 11, 2015, the entirety of both of which is hereby incorporated by reference.

FIELD OF THE INVENTION

The field of the disclosed technology is generally related to lubricating compositions comprising thioether-containing phenolic compounds.

BACKGROUND OF THE INVENTION

Recently, new engine tests like the Mack T13, have been developed to measure oxidation at higher temperatures than previous engine tests. It is believed that these new tests better simulate the higher temperatures experienced in modern heavy duty ("HD") diesel engines. These higher temperatures, however, place greater oxidative stress on engine oil formulations. Thus, treat rates of traditional engine oil antioxidants, including phenolic and aminic antioxidants are expected to increase. In the case of aminic antioxidants, the treat rates could increase as much as ten-fold.

The increase in treat rates may negatively affect the lubricants' performance in other areas such as wear, friction, soot deposits, acid build-up, corrosion, or seal wear, making it difficult to meet engine oil specifications for oxidation while also meeting the specification for other properties, such as deposits and acid build-up. As used herein, total base number ("TBN") values are measured by the methodology described in ASTM D2896 unless otherwise specifically noted.

SUMMARY OF THE INVENTION

It was surprisingly found, however, that thioether-substituted phenols ("thioether-phenol" or "thioether-phenols") showed improved antioxidant performance while reducing deposit formation compared to known phenolic antioxidants. Accordingly, in one embodiment, lubricating compositions comprising an oil of lubricating viscosity and a thioether-substituted phenol ("thioether-phenol") are disclosed. The thioether-phenol may comprise the reaction product of a thioether-substituted alcohol or thioether-substituted amine and a phenol with at least one pendant acyl group and may have a ratio of sulfur groups to phenol groups of at least 1:1.

In one embodiment, the thioether-phenol may have the structure as in Formula (I):

Formula (I)

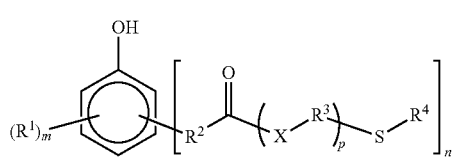

wherein m is an integer ranging from 0 to 3; n is an integer ranging from 1 to 2; p is an integer ranging from 1 to 20; each $R^1$ is independently hydrogen or a $C_1$-$C_{20}$ hydrocarbyl group, or when m is greater than 1, two of the hydrocarbyl groups, when taken together, may form a saturated or unsaturated ring containing 5 to 6 carbon atoms; $R^2$ is a $C_1$-$C_6$ hydrocarbyl group; $R^3$ is a $C_1$-$C_{20}$ hydrocarbyl group; $R^4$ is a $C_1$-$C_{32}$ hydrocarbyl group; X is O (an oxygen atom) or $NR^5$ (a nitrogen atom with a hydrocarbyl group); and $R^5$ is hydrogen or a $C_1$-$C_{24}$ hydrocarbyl group with the proviso that when X is $NR^5$, then p is 1.

In another embodiment, at least one $R^1$ may be a $C_1$-$C_4$ hydrocarbyl group. It yet another embodiment, $R^3$ may be a $C_1$-$C_{20}$ hydrocarbyl group, X is O (oxygen) and p is an integer ranging from 1 to 12.

In another embodiment, the lubricating composition may comprise a thioether-phenol having the structure as in Formula (II):

Formula (II)

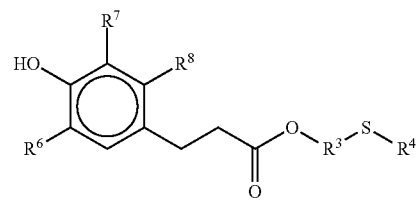

wherein $R^3$ is a $C_1$-$C_{20}$ hydrocarbyl group; $R^4$ is a $C_1$-$C_{32}$ hydrocarbyl group; $R^6$ is hydrogen or a $C_1$-$C_{12}$ hydrocarbyl group; and $R^7$ and $R^8$ are independently hydrogen or a $C_1$-$C_{20}$ hydrocarbyl group or, when taken together, $R^7$ and $R^8$ may form a saturated or unsaturated ring containing 5 to 6 carbon atoms.

In one embodiment, at least one of $R^6$ and $R^7$ may be a tert-butyl group. In yet another embodiment, both $R^6$ and $R^7$ may be a tert-butyl group. In another embodiment, $R^4$ may be a $C_1$-$C_{18}$ hydrocarbyl group. In yet another embodiment, $R^3$ may be a $C_2$-$C_4$ hydrocarbyl group.

In another embodiment, the thioether-phenol may comprise at least one of 2-(butylthio)ethyl 3-(3,5-di-tert-butyl-4-hydroxyphenyl)propanoate, 2-(butylthio)propyl 3-(3,5-di-tert-butyl-4-hydroxyphenyl)propanoate, 2-(butylthio)butyl 3-(3,5-di-tert-butyl-4-hydroxyphenyl)propanoate, 2-(hexylthio)ethyl 3-(3,5-di-tert-butyl-4-hydroxyphenyl)propanoate, 2-(hexylthio)propyl 3-(3,5-di-tert-butyl-4-hydroxyphenyl)propanoate, 2-(hexylthio)butyl 3-(3,5-di-tert-butyl-4-hydroxyphenyl)propanoate, 2-(octylthio)ethyl 3-(3,5-di-tert-butyl-4-hydroxyphenyl)propanoate, 2-(octylthio)propyl 3-(3,5-di-tert-butyl-4-hydroxyphenyl)propanoate, 2-(octylthio)butyl 3-(3,5-di-tert-butyl-4-hydroxyphenyl)propanoate, 2-(decylthio)ethyl 3-(3,5-di-tert-butyl-4-hydroxyphenyl)propanoate, 2-(decylthio)propyl 3-(3,5-di-tert-butyl-4-hydroxyphenyl)propanoate, 2-(decylthio)butyl 3-(3,5-di-tert-butyl-4-hydroxyphenyl)propanoate, 2-(dodecylthio)ethyl 3-(3,5-di-tert-butyl-4-hydroxyphenyl)propanoate, 2-(dodecylthio)propyl 3-(3,5-di-tert-butyl-4-hydroxyphenyl)propanoate, or 2-(dodecylthio)butyl 3-(3,5-di-tert-butyl-4-hydroxyphenyl)propanoate, or mixtures thereof. The lubricating composition may comprise from 0.01 wt % to 5 wt % of the thioether-phenol based on a total weight of the lubricating composition.

In one embodiment, the lubricating composition may further comprise at least one nitrogen-containing dispersant.

In other embodiments, the lubricating composition may further comprise at least one overbased detergent.

Methods of lubricating an internal combustion engine are also disclosed. The method may comprise contacting the internal combustion engine with a lubricating composition comprising a thioether-substituted phenol ("thioether-phenol") as described above. The thioether-phenol may be the reaction product of a thioether-substituted phenol or a thioether-substituted amine and a phenol with at least one pendant acyl group. The ratio of sulfur groups to phenol groups may be at least 1:1.

Uses of a thioether-phenol in a lubricating composition as described above are also disclosed. The thioether-phenol may be used to reduce oxidation, reduce deposit formation and/or aid in maintaining the total base number (TBN) of the lubricating composition.

Methods of reducing deposit formation and/or corrosion in an internal combustion engine are also disclosed. The methods may comprise contacting the internal combustion engine with a lubricating composition comprising a thioether-substituted phenol ("thioether-phenol") as described above.

DETAILED DESCRIPTION OF THE INVENTION

Each of the documents referred to above is incorporated herein by reference, including any prior applications, whether or not specifically listed above, from which priority is claimed. The mention of any document is not an admission that such document qualifies as prior art or constitutes the general knowledge of the skilled person in any jurisdiction. Except in the Examples, or where otherwise explicitly indicated, all numerical quantities in this description specifying amounts of materials, reaction conditions, molecular weights, number of carbon atoms, and the like, are to be understood as modified by the word "about." It is to be understood that the upper and lower amount, range, and ratio limits set forth herein may be independently combined. Similarly, the ranges and amounts for each element of the invention can be used together with ranges or amounts for any of the other elements.

As used herein, the transitional term "comprising," which is synonymous with "including," "containing," or "characterized by," is inclusive or open-ended and does not exclude additional, un-recited elements or method steps. However, in each recitation of "comprising" herein, it is intended that the term also encompass, as alternative embodiments, the phrases "consisting essentially of" and "consisting of," where "consisting of" excludes any element or step not specified and "consisting essentially of" permits the inclusion of additional un-recited elements or steps that do not materially affect the basic and novel characteristics of the composition or method under consideration.

Various features and embodiments are described below by way of non-limiting descriptions and examples. In one embodiment, lubricating compositions comprising an oil of lubricating viscosity and a thioether-substituted phenol ("thioether-phenol") are disclosed. The thioether-phenol comprises the reaction or condensation product of a thioether-substituted alcohol or thioether-substituted amine and a phenol with at least one pendant acyl group. The thioether-phenol may comprise the reaction product of a thioalcohol and a phenol.

Suitable thioether-substituted alcohols include, but are not limited to, 2-(butylthio) ethanol, 2-(butylthio) propanol, 2-(butylthio) butanol, 2-(hexylthio) ethanol, 2-(hexylthio) propanol, 2-(hexylthio) butanol, 2-(octylthio) ethanol, 2-(octylthio) propanol, 2-(octylthio) butanol, 2-(decylthio) ethanol, 2-(decylthio) propanol, 2-(decylthio) butanol, 2-(dodecylthio) ethanol, 2-(dodecylthio) propanol, 2-(dodecylthio) butanol, etc. Suitable phenols include, but are not limited to, 3-(3,5-di-tert-butyl-4-hydroxyphenyl)propanoic acid, 3-(3,5-di-tert-butyl-4-hydroxyphenyl)propanoic acid methylester, 3-(3,5-di-tert-butyl-4-hydroxyphenyl)propanoic acid ethylester, 3-(3,5-di-tert-butyl-4-hydroxyphenyl)propanoic acid propyl ester, 3-(3,5-di-tert-butyl-4-hydroxyphenyl)propanoic acid butyl ester, 3-(3,5-di-tert-butyl-4-hydroxyphenyl)propanoic acid hexylester, etc.

In one embodiment, the thioether-phenol may have a ratio of sulfur groups to phenol groups of at least 1:1. In other embodiments, the thioether-phenol may have a ratio of sulfur to phenol groups of at least 1:1 to 2:1.

In one embodiment, the thioether-phenol may have the structure as in Formula (I):

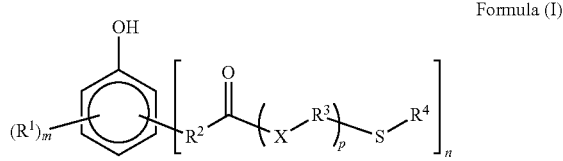

Formula (I)

wherein m is an integer ranging from 0 to 3; n is an integer ranging from 1 to 2; p is an integer ranging from 1 to 20; each $R^1$ is independently hydrogen or a $C_1$-$C_{20}$ hydrocarbyl group, or when m is greater than 1, two of the hydrocarbyl groups, when taken together, may form a saturated or unsaturated ring containing 5 to 6 carbon atoms; $R^2$ is a $C_1$-$C_6$ hydrocarbyl group; $R^3$ is a $C_1$-$C_{20}$ hydrocarbyl group; $R^4$ is a $C_1$-$C_{32}$ hydrocarbyl group; X is O (an oxygen atom) or $NR^5$ (a nitrogen atom with a hydrocarbyl group); and $R^5$ is hydrogen or a $C_1$-$C_{24}$ hydrocarbyl group with the proviso that when X is $NR^5$, then p is 1.

In another embodiment, at least one $R^1$ may be a $C_1$-$C_4$ hydrocarbyl group. It yet another embodiment, $R^3$ may be a $C_1$-$C_{20}$ hydrocarbyl group, X is O (oxygen) and p is an integer ranging from 1 to 12.

As used herein, the term "hydrocarbyl substituent" or "hydrocarbyl group" is used in its ordinary sense, which is well-known to those skilled in the art. Specifically, it refers to a group having a carbon atom directly attached to the remainder of the molecule and having predominantly hydrocarbon character. Examples of hydrocarbyl groups include:

hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form a ring);

substituted hydrocarbon substituents, that is, substituents containing non-hydrocarbon groups which, in the context of this invention, do not alter the predominantly hydrocarbon nature of the substituent (e.g., halo (especially chloro and fluoro), hydroxy, alkoxy, mercapto, alkylmercapto, nitro, nitroso, and sulfoxy);

hetero substituents, that is, substituents which, while having a predominantly hydrocarbon character, in the context of this invention, contain other than carbon in a ring or chain otherwise composed of carbon atoms and encompass substituents as pyridyl, furyl, thienyl and imidazolyl. Heteroatoms include sulfur, oxygen, and nitrogen. In general, no more than two, or no more than one, non-hydrocarbon substituent will be present for every ten carbon atoms in the hydrocarbyl group; alternatively, there may be no non-hydrocarbon substituents in the hydrocarbyl group.

In yet another embodiment, the thioether-phenol may have the structure as in Formula (II):

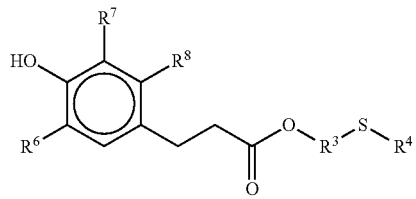

Formula (II)

wherein $R^3$ is a $C_1$-$C_{20}$ hydrocarbyl group; $R^4$ is a $C_1$-$C_{32}$ hydrocarbyl group; $R^6$ is hydrogen or a $C_1$-$C_{12}$ hydrocarbyl group; and $R^7$ and $R^8$ are independently hydrogen or a $C_1$-$C_{20}$ hydrocarbyl group or, when taken together, $R^7$ and $R^8$ may form a saturated or unsaturated ring containing 5 to 6 carbon atoms.

In one embodiment, at least one of $R^6$ and $R^7$ may be a tert-butyl group. In yet another embodiment, both $R^6$ and $R^7$ may be a tert-butyl group. In another embodiment, $R^4$ may be a $C_1$-$C_{18}$ hydrocarbyl group. In yet another embodiment, $R^3$ may be a $C_2$-$C_4$ hydrocarbyl group.

In another embodiment, the thioether-phenol may comprise at least one of 2-(butylthio)ethyl 3-(3,5-di-tert-butyl-4-hydroxyphenyl)propanoate, 2-(butylthio)propyl 3-(3,5-di-tert-butyl-4-hydroxyphenyl)propanoate, 2-(butylthio)butyl 3-(3,5-di-tert-butyl-4-hydroxyphenyl)propanoate, 2-(hexylthio)ethyl 3-(3,5-di-tert-butyl-4-hydroxyphenyl)propanoate, 2-(hexylthio)propyl 3-(3,5-di-tert-butyl-4-hydroxyphenyl)propanoate, 2-(hexylthio)butyl 3-(3,5-di-tert-butyl-4-hydroxyphenyl)propanoate, 2-(octylthio)ethyl 3-(3,5-di-tert-butyl-4-hydroxyphenyl)propanoate, 2-(octylthio)propyl 3-(3,5-di-tert-butyl-4-hydroxyphenyl)propanoate, 2-(octylthio)butyl 3-(3,5-di-tert-butyl-4-hydroxyphenyl)propanoate, 2-(decylthio)ethyl 3-(3,5-di-tert-butyl-4-hydroxyphenyl)propanoate, 2-(decylthio)propyl 3-(3,5-di-tert-butyl-4-hydroxyphenyl)propanoate, 2-(decylthio)butyl 3-(3,5-di-tert-butyl-4-hydroxyphenyl)propanoate, 2-(dodecylthio)ethyl 3-(3,5-di-tert-butyl-4-hydroxyphenyl)propanoate, 2-(dodecylthio)propyl 3-(3,5-di-tert-butyl-4-hydroxyphenyl)propanoate, or 2-(dodecylthio)butyl 3-(3,5-di-tert-butyl-4-hydroxyphenyl)propanoate, or mixtures thereof.

In other embodiments, the thioether-phenol may comprise at least one thioether-phenol having one of the following structures.

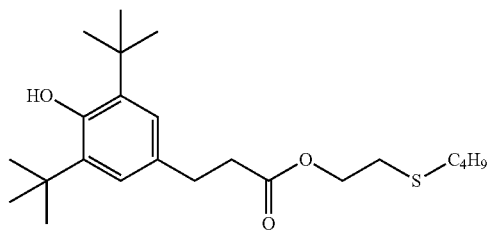

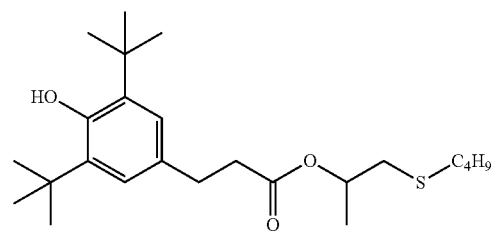

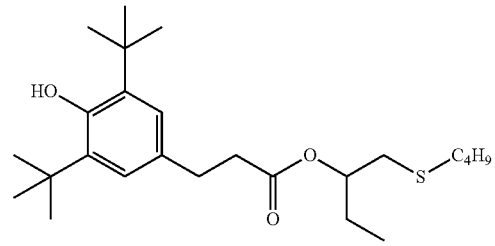

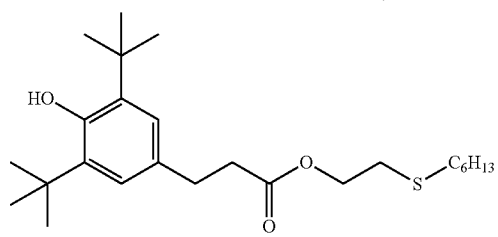

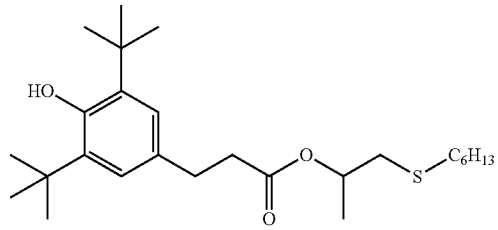

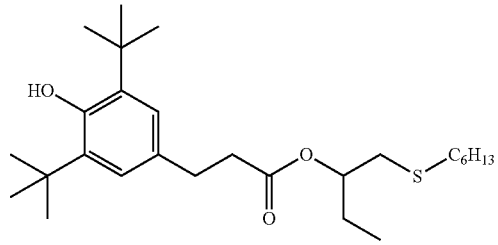

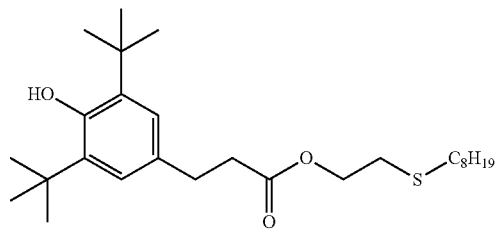

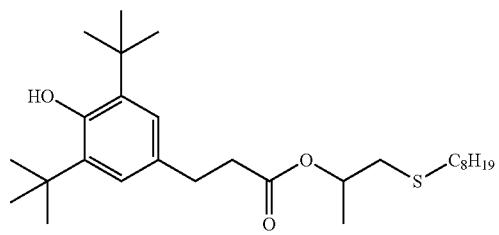

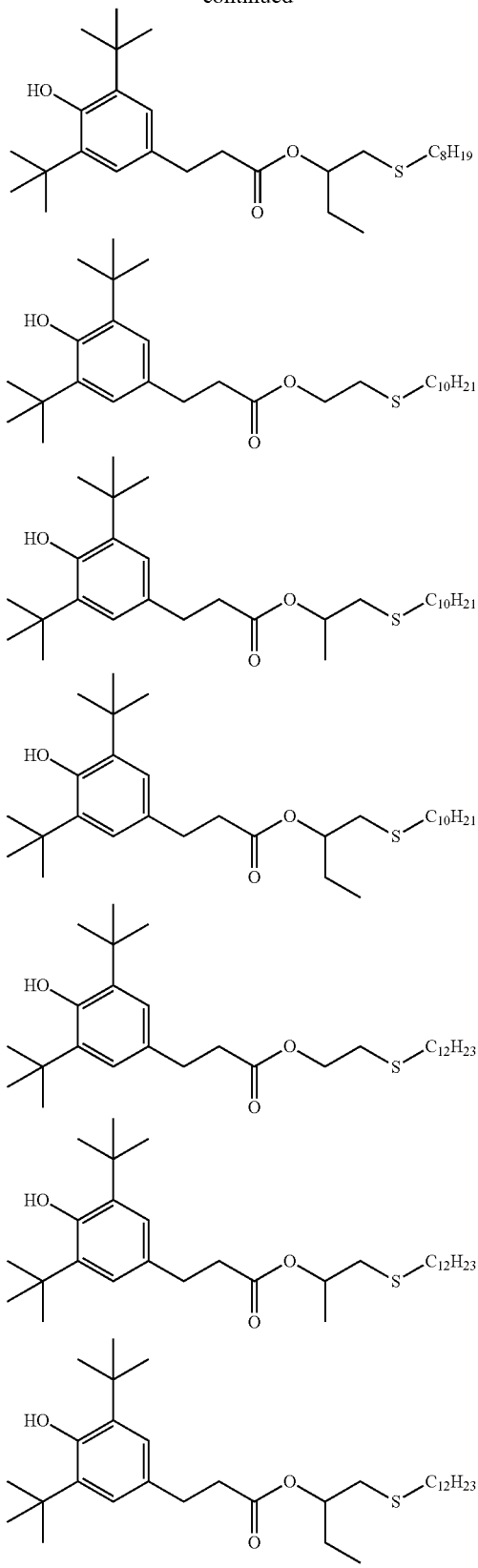

The lubricating composition may comprise from 0.01 wt % to 5 wt % of the thioether-phenol based on a total weight of the lubricating composition. Alternatively the thioether-phenol may be present in the following ranges: 0.01 to 3 wt %; 0.01 to 1 wt %; 0.01 to 0.5 wt %; or 0.05 to 0.1 wt %. The amount of each chemical component described is presented exclusive of any solvent or diluent oil, which may be customarily present in the commercial material, that is, on an active chemical basis, unless otherwise indicated. However, unless otherwise indicated, each chemical or composition referred to herein should be interpreted as being a commercial grade material which may contain the isomers, by-products, derivatives, and other such materials which are normally understood to be present in the commercial grade.

The lubricating composition may comprise one or more additives in addition to the antioxidant described above. In one embodiment, the lubricating composition may further comprise at least one nitrogen-containing dispersant. In other embodiments, the lubricating composition may further comprise at least one overbased detergent. In yet other embodiments, the lubricating composition may further comprise a corrosion inhibitor.

The lubricating composition may include an antiwear agent. In one embodiment, the antiwear agent may comprise phosphorus that is present in an amount such that the lubricating composition has at least 300 ppm phosphorus based on a total weight of the lubricating composition.

In another embodiment, the lubricating composition may comprise at least one boron-containing compound. Exemplary boron-containing compounds include, but are not limited to, borate esters, borate alcohols, or combinations thereof.

Methods of lubricating an internal combustion engine are also disclosed. The method may comprise contacting the internal combustion engine with a lubricating composition comprising a thioether-substituted phenol ("thioether-phenol") as described above. The thioether-phenol may be the reaction product of a thioether-substituted phenol or a thioether-substituted amine and a phenol with at least one pendant acyl group. The ratio of sulfur groups to phenol groups may be at least 1:1.

Uses of a thioether-phenol in a lubricating composition as described above are also disclosed. The thioether-phenol may be used to reduce oxidation, reduce deposit formation and/or aid in maintaining the total base number (TBN) of the lubricating composition.

Methods of reducing deposit formation and/or corrosion in an internal combustion engine are also disclosed. The methods may comprise contacting the internal combustion engine with a lubricating composition comprising a thioether-substituted phenol ("thioether-phenol") as described above.

Oils of Lubricating Viscosity

The lubricating compositions comprising thioether-phenol described herein may be used in an oil of lubricating viscosity. Such oils include natural and synthetic oils, oil derived from hydrocracking, hydrogenation, and hydrofinishing, unrefined, refined, re-refined oils or mixtures thereof. A more detailed description of unrefined, refined and re-refined oils is provided in International Publication WO2008/147704, paragraphs [0054] to [0056] (a similar disclosure is provided in US Patent Application 2010/197536, see [0072] to [0073]). A more detailed description of natural and synthetic lubricating oils is described in paragraphs [0058] to [0059] respectively of WO2008/147704 (a similar disclosure is provided in US Patent Application 2010/197536, see [0075] to [0076]). Synthetic oils may also be produced by Fischer-Tropsch reactions and typically may be hydroisomerized Fischer-Tropsch hydrocarbons or waxes. In one embodiment, oils may be prepared by a Fischer-Tropsch gas-to-liquid synthetic procedure as well as other gas-to-liquid oils.

Oils of lubricating viscosity may also be defined as specified in the September 2011 version of "Appendix E-API Base Oil Interchangeability Guidelines for Passenger Car Motor Oils and Diesel Engine Oils", section 1.3 Subheading 1.3. "Base Stock Categories". In one embodiment the oil of lubricating viscosity may be an API Group II or Group III oil. In one embodiment, the oil of lubricating viscosity may be an API Group I oil.

The amount of the oil of lubricating viscosity present is typically the balance remaining after subtracting from 100 wt % the sum of the amount of the compound of the invention and the other performance additives.

The lubricating composition may be in the form of a concentrate and/or a fully formulated lubricant. If the lubricating composition of the invention (comprising the additives disclosed herein) is in the form of a concentrate which may be combined with additional oil to form, in whole or in part, a finished lubricant), the ratio of the of these additives to the oil of lubricating viscosity and/or to diluent oil include the ranges of 1:99 to 99:1 by weight, or 80:20 to 10:90 by weight.

Other Performance Additives

The composition optionally comprises other performance additives. The other performance additives may include at least one of metal deactivators, viscosity modifiers, detergents, friction modifiers, antiwear agents, corrosion inhibitors, dispersants, dispersant viscosity modifiers, extreme pressure agents, antioxidants (other than the thioether-phenols described above), foam inhibitors, demulsifiers, pour point depressants, seal swelling agents and mixtures thereof. These other performance additives may be in addition to the additives of the disclosed technology. For example, additives may be corrosion inhibitors, antiwear agents and/or antioxidants present in the lubricating composition in addition to those described in other embodiments of the disclosed technology.

Accordingly, in one embodiment, the disclosed technology provides a lubricating composition further comprising at least one of a dispersant, an antiwear agent, a dispersant viscosity modifier, a friction modifier, a viscosity modifier (typically an olefin copolymer such as an ethylene-propylene copolymer), an antioxidant (including phenolic and aminic antioxidants), an overbased detergent (including overbased sulfonates and phenates), an extreme pressure agent, a foam inhibitor, a demulsifier, a pour point depressant, a seal swelling agent, or mixtures thereof.

The dispersant may be a succinimide dispersant, or mixtures thereof. In one embodiment, the dispersant may be present as a single dispersant. In one embodiment, the dispersant may be present as a mixture of two or three different dispersants, wherein at least one may be a succinimide dispersant.

The succinimide dispersant may be derived from at least one aliphatic polyamine. The aliphatic polyamine may be an ethylenepolyamine, a propylenepolyamine, a butylenepolyamine, or mixtures thereof. In one embodiment, the aliphatic polyamine may be ethylenepolyamine. In one embodiment, the aliphatic polyamine may be selected from the group consisting of ethylenediamine, diethylenetriamine, triethylenetetramine, tetraethylenepentamine, pentaethylenehexamine, polyamine still bottoms, and mixtures thereof.

The dispersant may also be derived from a material having an aromatic amine. The aromatic amine that may be useful is disclosed in International publications WO2010/062842 and WO2009/064685 (a similar disclosure is provided in US 2010/298185). The aromatic amine of WO2009/064685 is typically reacted with isatoic anhydride.

The aromatic amine may typically not be a heterocycle. The aromatic amine may include aniline, nitroaniline, aminocarbazole, 4-aminodiphenylamine (ADPA), and coupling products of ADPA. In one embodiment, the amine may be 4-aminodiphenylamine (ADPA), or coupling products of ADPA. The aromatic amine may include bis[p-(p-aminoanilino)phenyl]-methane, 2-(7-amino-acridin-2-ylmethyl)-N-4-{4-[4-(4-amino-phenylamino)-benzyl]-phenyl}-benzene-1,4-diamine, N-{4-[4-(4-amino-phenylamino)-benzyl]-phenyl}-2-[4-(4-amino-phenylamino)-cyclohexa-1,5-dienylmethyl]-benzene-1,4-diamine, N-[4-(7-amino-acridin-2-ylmethyl)-phenyl]-benzene-1,4-diamine, or mixtures thereof.

The dispersant may be an N-substituted long chain alkenyl succinimide. Examples of N-substituted long chain alkenyl succinimide include polyisobutylene succinimide. Typically, the polyisobutylene from which polyisobutylene succinic anhydride is derived has a number average molecular weight of 350 to 5000, or 550 to 3000 or 750 to 2500. Succinimide dispersants and their preparation are disclosed, for instance, in U.S. Pat. Nos. 3,172,892, 3,219,666, 3,316,177, 3,340,281, 3,351,552, 3,381,022, 3,433,744, 3,444,170, 3,467,668, 3,501,405, 3,542,680, 3,576,743, 3,632,511, 4,234,435, Re 26,433, and U.S. Pat. Nos. 6,165,235, 7,238,650 and EP Patent Application 0 355 895 A.

The dispersant may also be post-treated by conventional methods by a reaction with any of a variety of agents. Among these are boron compounds (such as boric acid & borate esters), urea, thiourea, dimercaptothiadiazoles, carbon disulfide, aldehydes, ketones, carboxylic acids, hydrocarbon-substituted succinic anhydrides, maleic anhydride, nitriles, epoxides, and phosphorus compounds.

The dispersant may be present at 0.1 wt % to 10 wt %, or 2.5 wt % to 6 wt %, or 3 wt % to 5 wt % of the lubricating composition.

In one embodiment, the lubricating composition of the disclosed technology further comprises a dispersant viscosity modifier. The dispersant viscosity modifier may be present at 0 wt % to 5 wt %, or 0 wt % to 4 wt %, or 0.05 wt % to 2 wt % of the lubricating composition.

The dispersant viscosity modifier may include functionalized polyolefins, for example, ethylene-propylene copolymers that have been functionalized with an acylating agent such as maleic anhydride and an amine; polymethacrylates functionalized with an amine, or styrene-maleic anhydride copolymers reacted with an amine. More detailed description of dispersant viscosity modifiers are disclosed in International Publication WO2006/015130 or U.S. Pat. Nos. 4,863,623; 6,107,257; 6,107,258; and 6,117,825. In one embodiment, the dispersant viscosity modifier may include those described in U.S. Pat. No. 4,863,623 (see column 2, line 15 to column 3, line 52) or in International Publication WO2006/015130 (see page 2, paragraph [0008] and preparative examples are described paragraphs [0065] to [0073]).

In one embodiment, the dispersant viscosity modifier may include those described in U.S. Pat. No. 7,790,661 column 2, line 48 to column 10, line 38. The dispersant viscosity modifier of 7,790,661 includes (a) a polymer comprising carboxylic acid functionality or a reactive equivalent thereof, the polymer having a number average molecular weight of greater than 5,000; and (b) an amine component comprising at least one aromatic amine containing at least one amino group capable of condensing with said carboxylic acid functionality to provide a pendant group and at least one additional group comprising at least one nitrogen, oxygen, or sulfur atom, in which the aromatic amine is selected from the group consisting of (i) a nitro-substituted aniline, (ii) amines comprising two aromatic moieties linked by a —C(O)NR$^{11}$— group, a —C(O)O— group, an —O— group, an —N—N— group, or an —SO$_2$— group, wherein R$^{11}$ is hydrogen or hydrocarbyl, one of the aromatic moieties bearing the condensable amino group, (iii) an aminoquinoline, (iv) an aminobenzimidazole, (v) an N,N-dialkylphenylenediamine, and (vi) a ring-substituted benzylamine.

In one embodiment, the disclosed technology can be a lubricating composition further comprising a molybdenum compound. The molybdenum compound may be selected from the group consisting of molybdenum dialkyldithiophosphates, molybdenum dithiocarbamates, amine salts of molybdenum compounds, and mixtures thereof. The molybdenum compound may provide the lubricating composition with 0 to 1000 ppm, or 5 to 1000 ppm, or 10 to 750 ppm, or 5 ppm to 300 ppm, or 20 ppm to 250 ppm of molybdenum.

In one embodiment, the disclosed technology can be a lubricating composition further including an overbased detergent. Overbased detergents are known in the art. The overbased detergent may be selected from the group consisting of non-sulfur containing phenates, sulfur containing phenates, sulfonates, salixarates, salicylates, and mixtures thereof.

The overbased detergent may also include "hybrid" detergents formed with mixed surfactant systems including phenate and/or sulfonate components, e.g., phenate/salicylates, sulfonate/phenates, sulfonate/salicylates, sulfonates/phenates/salicylates, as described, for example, in U.S. Pat. Nos. 6,429,178; 6,429,179; 6,153,565; and 6,281,179. Where, for example, a hybrid sulfonate/phenate detergent is employed, the hybrid detergent would be considered equivalent to amounts of distinct phenate and sulfonate detergents introducing like amounts of phenate and sulfonate soaps, respectively.

Typically an overbased detergent may be a sodium, calcium or magnesium salt of the phenates, sulfur containing phenates, sulfonates, salixarates and salicylates. Overbased phenates and salicylates typically have a total base number of 180 to 450 TBN as measured using ASTM D2896. Overbased sulfonates typically have a total base number of 250 to 600, or 300 to 500. In one embodiment, the sulfonate detergent may be a predominantly linear alkylbenzene sulfonate detergent having a metal ratio of at least 8 as is described in paragraphs [0026] to [0037] of US Patent Application 2005065045 (and granted as U.S. Pat. No. 7,407,919). Linear alkyl benzenes may have the benzene ring attached anywhere on the linear chain, usually at the 2, 3, or 4 position, or mixtures thereof. The predominantly linear alkylbenzene sulfonate detergent may be particularly useful for assisting in improving fuel economy. In one embodiment, the sulfonate detergent may be a metal salt of one or more oil-soluble alkyl toluene sulfonate compounds as disclosed in paragraphs [0046] to [0053] of US Patent Application 2008/0119378. The overbased detergent may be present at 0 wt % to 15 wt %, or 1 wt % to 10 wt %, or 3 wt % to 8 wt %. For example, in a heavy duty diesel engine, the detergent may be present at or 3 wt % to 5 wt % of the lubricating composition. For a passenger car engine, the detergent may be present at 0.2 wt % to 1 wt % of the lubricating composition.

In one embodiment, the lubricating composition includes at least one antioxidant. The antioxidant may be present at 0 wt % to 15 wt %, or 0.1 wt % to 10 wt %, or 0.5 wt % to 5 wt % of the lubricating composition.

Antioxidants include sulfurized olefins, alkylated diphenylamines (typically dinonyl diphenylamine, octyl diphenylamine, dioctyl diphenylamine), phenyl-α-naphthylamine (PANA), hindered phenols, molybdenum compounds (such as molybdenum dithiocarbamates), or mixtures thereof.

The hindered phenol antioxidant often contains a secondary butyl and/or a tertiary butyl group as a sterically hindering group. The phenol group may be further substituted with a hydrocarbyl group (typically linear or branched alkyl) and/or a bridging group linking to a second aromatic group. Examples of suitable hindered phenol antioxidants include 2,6-di-tert-butylphenol, 4-methyl-2,6-di-tert-butylphenol, 4-ethyl-2,6-di-tert-butylphenol, 4-propyl-2,6-di-tert-butylphenol or 4-butyl-2,6-di-tert-butylphenol, or 4-dodecyl-2,6-di-tert-butylphenol. In one embodiment, the hindered phenol antioxidant may be an ester and may include, e.g., Irganox™ L-135 from Ciba. A more detailed description of suitable ester-containing hindered phenol antioxidant chemistry is found in U.S. Pat. No. 6,559,105.

Examples of suitable friction modifiers include long chain fatty acid derivatives of amines, fatty esters, or fatty epoxides; fatty imidazolines such as condensation products of carboxylic acids and polyalkylene-polyamines; amine salts of alkylphosphoric acids; fatty alkyl tartrates; fatty alkyl tartrimides; or fatty alkyl tartramides.

Friction modifiers may also encompass materials such as sulfurized fatty compounds and olefins, molybdenum dialkyldithiophosphates, molybdenum dithiocarbamates, sunflower oil or monoester of a polyol and an aliphatic carboxylic acid.

In one embodiment, the friction modifier may comprise at least one of long chain fatty acid derivatives of amines, long chain fatty esters, or long chain fatty epoxides; fatty imidazolines; amine salts of alkylphosphoric acids; fatty alkyl tartrates; fatty alkyl tartrimides; and fatty alkyl tartramides. The friction modifier may be present at 0 wt % to 6 wt %, or 0.05 wt % to 4 wt %, or 0.1 wt % to 2 wt % of the lubricating composition. In one embodiment, the lubricating composition may be free of long chain fatty esters (typically glycerol monooleate).

As used herein, the term "fatty alkyl" or "fatty" in relation to friction modifiers means a carbon chain having 10 to 22 carbon atoms, typically a straight carbon chain. Alternatively, the fatty alkyl may be a mono branched alkyl group, with branching typically at the β-position. Examples of mono branched alkyl groups include 2-ethylhexyl, 2-propylheptyl or 2-octyldodecyl.

In one embodiment, the friction modifier may comprise at least one of long chain fatty acid derivatives of amines, fatty esters, or fatty epoxides; fatty alkyl citrates, fatty alkyl tartrates; fatty alkyl tartrimides; and fatty alkyl tartramides.

In one embodiment, the friction modifier may be a long chain fatty acid ester. In another embodiment, the long chain fatty acid ester may be a mono-ester and in another embodiment the long chain fatty acid ester may be a triglyceride.

Other performance additives such as corrosion inhibitors include those described in paragraphs 5 to 8 of WO2006/047486, octyl octanamide, condensation products of dodecenyl succinic acid or anhydride and a fatty acid such as oleic acid with a polyamine. In one embodiment, the corrosion inhibitors include the Synalox® (a registered trademark of The Dow Chemical Company) corrosion inhibitor. The Synalox® corrosion inhibitor may be a homopolymer or copolymer of propylene oxide. The Synalox® corrosion inhibitor is described in more detail in a product brochure with Form No. 118-01453-0702 AMS, published by The Dow Chemical Company. The product brochure is entitled "SYNALOX Lubricants, High-Performance Polyglycols for Demanding Applications."

Metal deactivators include derivatives of benzotriazoles (typically tolyltriazole), dimercaptothiadiazole derivatives, 1,2,4-triazoles, benzimidazoles, 2-alkyldithiobenzimidazoles, or 2-alkyldithiobenzothiazoles.

In one embodiment, the corrosion inhibitors and metal deactivators described above may be used in addition to the azole-acrylic adducts described herein. In yet another embodiment, the corrosion inhibitors and metal deactivators described above may be substituted with the azole-acrylic adducts described herein.

Foam inhibitors include polysiloxane or copolymers of ethyl acrylate and 2-ethylhexyl acrylate and optionally vinyl acetate. Demulsifiers include trialkyl phosphates, polyethylene glycols, polyethylene oxides, polypropylene oxides and (ethylene oxide-propylene oxide) polymers. Pour point depressants include esters of maleic anhydride-styrene, polymethacrylates, polyacrylates or polyacrylamides.

In different embodiments, the lubricating composition may have a composition as described in Table 1 below. The weight percents (wt %) are on an actives basis.

TABLE 1

| Additive | Embodiments (wt %) | | |
|---|---|---|---|
| | A | B | C |
| Thioether-phenol Antioxidant | 0.01 to 5 | 0.01 to 3 | 0.01 to 1 |
| Boron-Containing Compound | 0.0 to 8 | 0.05 to 4 | 0.05 to 3 |
| Nitrogen-Containing Dispersant | 0.05 to 12 | 0.5 to 8 | 1 to 5 |
| Dispersant Viscosity Modifier | 0 to 5 | 0 to 4 | 0.05 to 2 |
| Overbased Detergent | 0 to 15 | 0.1 to 8 | 0.5 to 3 |
| Corrosion Inhibitor | 0 to 3 | 0.01 to 3 | 0.01 to 3 |
| Phosphorous Antiwear Agent | 0.1 to 15 | 0.2 to 6 | 0.3 to 2 |
| Friction Modifier | 0 to 6 | 0.05 to 4 | 0.1 to 2 |
| Viscosity Modifier | 0 to 10 | 0.5 to 8 | 1 to 6 |
| Any Other Performance Additive | 0 to 10 | 0 to 8 | 0 to 6 |
| Oil of Lubricating Viscosity | Balance to 100% | Balance to 100% | Balance to 100% |

INDUSTRIAL APPLICATION

The lubricating composition may be utilized in an internal combustion engine. The engine or engine components may be made of an alloy comprising lead or copper. The engine components may have a surface of steel or aluminum (typically a surface of steel).

An aluminum surface may be derived from an aluminum alloy that may be a eutectic or hyper-eutectic aluminum alloy (such as those derived from aluminum silicates, aluminum oxides, or other ceramic materials). The aluminum surface may be present on a cylinder bore, cylinder block, or piston ring having an aluminum alloy, or aluminum composite.

The internal combustion engine may or may not have an Exhaust Gas Recirculation system. The internal combustion engine may be fitted with an emission control system or a turbocharger. Examples of the emission control system include diesel particulate filters (DPF), or systems employing selective catalytic reduction (SCR).

In one embodiment, the internal combustion engine may be a diesel fueled engine (typically a heavy duty diesel engine), a gasoline fueled engine, a natural gas-fueled engine or a mixed gasoline/alcohol fueled engine. In one embodiment, the internal combustion engine may be a diesel fueled engine and in another embodiment a gasoline fueled engine. In one embodiment, the internal combustion engine may be a heavy duty diesel engine.

The internal combustion engine may be a 2-stroke or 4-stroke engine. Suitable internal combustion engines include marine diesel engines, aviation piston engines, low-load diesel engines, and automobile and truck engines.

The lubricant composition for an internal combustion engine may be suitable for any engine lubricant irrespective of the sulfur, phosphorus or sulfated ash (ASTM D-874) content. The lubricating composition may be characterized as having at least one of (i) a sulfur content of 0.2 wt % to 0.4 wt % or less, (ii) a phosphorus content of 0.08 wt % to 0.15 wt %, and (iii) a sulfated ash content of 0.5 wt % to 1.5 wt % or less. The lubricating composition may be characterized as having (i) a sulfur content of 0.5 wt % or less, (ii) a phosphorus content of 0.1 wt % or less, and (iii) a sulfated ash content of 0.5 wt % to 1.5 wt % or less.

In one embodiment, the lubricating composition may be characterized as having a sulfated ash content of 0.5 wt % to 1.2 wt %.

It is known that some of the materials described above may interact in the final formulation, so that the components of the final formulation may be different from those that are initially added. For instance, metal ions (of, e.g., a detergent) can migrate to other acidic or anionic sites of other molecules. The products formed thereby, including the products formed upon employing the disclosed compositions, may not be susceptible of easy description. Nevertheless, all such modifications and reaction products are included within the scope of the present invention and the disclosed compositions encompass products formed by admixing the components and/or materials described above.

The following examples provide illustrations of the invention. These examples are non-exhaustive and are not intended to limit the scope of the invention.

EXAMPLES

Preparation of Thioether-Phenols

The following examples show non-limiting techniques to prepare thioether-phenols as described above.

Example A-1

A 2-L flask is charged with 2-(dodecylthio) ethanol (453 g, 1 mole), butyl 3-(3,5-di-tert-butyl-4-hydroxyphenyl) propanoate (627 g, 1.02 mole), and titanium butoxide (Ti(OBu)$_4$) (1.6 g, 0.0025 mole). The mixture is heated to 185° C. with stirring. The mixture is held at 185° C. to allow the components to react. Butanol is removed during the reaction process. Once the theoretical amount of butanol is collected (after about 7 hrs) the mixture is cooled, and the product is collected as a brown liquid.

Example A-2

A 2-L flask is charged with 2-(dodecylthio) butanol (1 eq), butyl 3-(3,5-di-tert-butyl-4-hydroxyphenyl) propanoate (1.02 eq), and titanium butoxide (Ti(OBu)$_4$) (0.0025 eq). The mixture is heated to 185° C. with stirring. The mixture is held at 185° C. to allow the components to react. Butanol is removed during the reaction process. Once the theoretical amount of butanol is collected (after about 7 hrs) the mixture is cooled, and the product is collected as a brown liquid.

Lubricant Examples EX0 to EX5

A series of 5W-30 engine lubricants of lubricating viscosity are prepared using conventional additives including polymeric viscosity modifiers, ashless succinimide dispersants, overbased detergents, antioxidants (combination of phenolic ester, diarylamine, and sulfurized olefin), zinc dialkyldithiophosphate (ZDDP), as well as other performance additives. All of the lubricants are prepared from a common formulation as follows in Table 2.

TABLE 2

Lubricating Oil Composition Base Formulation[1]

|  | Baseline (wt %) |
|---|---|
| Group II Base Oil | Balance to 100% |
| Overbased detergent[2] | 0.77 |
| Zinc dialkyldithiophosphate | 0.86 |
| Antioxidant | 1.85 |
| Active Dispersant[3] | 6.23 |
| Viscosity Modifier | 1.12 |
| Additional additives[4] | 0.18 |
| % Phosphorus | 0.75 |

[1]All concentrations are on an oil free (i.e. active basis)
[2]Ca alkylsulfonates.
[3]2000 $M_n$ PIB succinimide dispersants
[4]Additional additives include friction modifiers, foam inhibitors. etc.

The thioether-phenols of Examples A-1 and A-2 are then added to the baseline oil in the amounts shown in Table 3. The amounts are based on a total weight of the lubricating oil composition on an actives basis.

TABLE 3

Lubricating Oil Composition Formulations

| Examples | A-1 (wt %) | A-2 (wt %) |
|---|---|---|
| BL1 | | |
| EX1 | 0.78 | |
| EX2 | | 0.78 |

The lubricating oil compositions in Table 3 are evaluated using Pressure Differential Scanning Calorimetry (PDSC), Micro Coking Test (MCT), and Komatsu Hot Tube (KHT) oxidation bench tests.

PDSC evaluates the oxidation resistance or stability of a lubricating oil by measuring the oxidation induction time (OIT). The OIT is the time between the start of the oil's exposure to oxygen and the onset of oxidation under isothermic conditions. Thus, the longer the OIT, the more resistant the oil is to oxidation. The PDSC data are obtained using the CEC L-85-99 test procedures for predicting lubricant performance in heavy duty diesel engines.

The MCT evaluates the tendency of the lubricant to form carbon deposits or residue as the lubricant evaporates or thermally degrades. A small sample of the oil is placed on a metal plate. Different spots on the metal plate are then heated to 280° C. ("hot temperature") and 230° C. ("cold temperature") respectively. The metal plate is then visually inspected for carbon deposits or residue and compared to a standard. A rating with a value ranging from 1 to 10 is then assigned to each sample, with 1 having the most residue and 10 having the least amount of residue. Thus, in MCT, a higher rating means better deposit control performance. Details about the MCT may be found in the standardized procedure titled "Microcoking Test for Automotive Lubricants", GFC Lu-27-A-13 Issue 2.

For the KHT test, glass tubes are inserted through an aluminum heater block and heated to 280° C. The test sample is then pumped via a syringe pump through the glass tubes for 16 hours at a flow rate of 0.31 cm3/hr, along with an air flow of 10 cm3/min. At the end of the test, the tubes are rinsed and rated visually on a scale of 0 to 10, with 0 being a black tube and 10 being a clean tube.

KHT measures the deposit formation tendency of the lubricant at high temperature conditions. In KHT, a high rating means better deposit control performance. The results obtained for each lubricant are shown in Table 4.

TABLE 4

| Example | KHT 280° C. | L-85-99 OIT min | MCT |
|---|---|---|---|
| BL1 | 2 | 115 | 6.64 |
| EX1 | 7 | 145 | 8.67 |
| EX2 | 7 | 138 | 7.09 |

The results show that the lubricating compositions comprising the disclosed thioether-phenols provided improved antioxidation performance while reducing deposit formation compared to the baseline formulation (BL1).

Lubricant Examples EX3 to EX4

A second series of 5W-30 engine lubricants of lubricating viscosity are prepared using conventional additives including polymeric viscosity modifiers, ashless succinimide dispersants, overbased detergents, antioxidants (combination of phenolic ester, diarylamine, and sulfurized olefin), zinc dialkyldithiophosphate (ZDDP), as well as other performance additives. All of the lubricants are prepared from a common formulation as follows in Table 5.

TABLE 5

Lubricating Oil Composition Base Formulation[1]

|  | Baseline |
|---|---|
| Group II Base Oil | Balance to 100% |
| Overbased detergent[2] | 0.77 |
| Zinc dialkyldithiophosphate | 0.86 |
| Antioxidant | 0.85 |
| Active Dispersant[3] | 6.23 |
| Viscosity Modifier | 1.12 |
| Additional additives[4] | 0.18 |
| % Phosphorus | 0.75 |

[1]All concentrations are on an oil free (i.e. active basis)
[2]Ca alkylsulfonates.
[3]2000 Mn PIB succinimide dispersants
[4]Additional additives include friction modifiers, foam inhibitors. etc.

A commercially available phenolic antioxidant (Irganox L-135) and the thioether-phenols of Examples A-1 and A-2 are then added to the baseline oil in the amounts shown in Table 6. The amounts are based on a total weight of the lubricating oil composition on an actives basis.

TABLE 6

Lubricating Oil Composition Formulations

|  | Irganox L-135 | A-1 | A-2 |
|---|---|---|---|
| Comp 1 | 1 | | |
| EX3 | | 1 | |
| EX4 | | | 1 |

The lubricating oil compositions in Table 6 are evaluated using Pressure Differential Scanning Calorimetry (PDSC), Micro Coking Test (MCT), and Komatsu Hot Tube (KHT) oxidation bench tests. The results obtained for each lubricant are shown in Table 7.

TABLE 7

| Example | KHT 280° C. | L-85-99 OIT min | MCT |
|---------|-------------|-----------------|------|
| Comp1   | 2           | 115             | 6.64 |
| EX3     | 7           | 160             | 8.11 |
| EX4     | 5           | 141             | 7.34 |

The results show that the lubricating compositions comprising the disclosed thioether-phenols provided improved antioxidation performance while reducing deposit formation compared to the comparative formulation (Comp1) comprising the commercial phenolic antioxidant, Irganox L-135.

Lubricant Examples EX5 to EX6

A third series of 5W-30 engine lubricants of lubricating viscosity are prepared using conventional additives including polymeric viscosity modifiers, ashless succinimide dispersants, overbased detergents, antioxidants (combination of phenolic ester, diarylamine, and sulfurized olefin), zinc dialkyldithiophosphate (ZDDP), as well as other performance additives. All of the lubricants are prepared from a common formulation as follows in Table 8.

TABLE 8

Lubricating Oil Composition Base Formulation[1]

|                            | Baseline       |
|----------------------------|----------------|
| Group II Base Oil          | Balance to 100% |
| Overbased detergent[2]     | 1.0            |
| Zinc dialkyldithiophosphate| 0.86           |
| Antioxidant                | 0.85           |
| Active Dispersant[3]       | 6.23           |
| Viscosity Modifier         | 1.12           |
| Additional additives[4]    | 0.18           |
| % Phosphorus               | 0.75           |

[1]All concentrations are on an oil free (i.e. active basis)
[2]A mixture of Ca alkylsulfonates & Ca alkylphenates.
[3]2000 Mn PIB succinimide dispersants
[4]Additional additives include friction modifiers, foam inhibitors. etc.

A commercially available phenolic antioxidant (Irganox L-135) and the thioether-phenols of Examples A-1 and A-2 are then added to the baseline oil in the amounts shown in Table 9. The amounts are based on a total weight of the lubricating oil composition on an actives basis.

TABLE 9

Lubricating Oil Composition Formulations

|       | Irganox L-135 | A-1 | A-2 |
|-------|---------------|-----|-----|
| Comp2 | 1             |     |     |
| EX5   |               | 1   |     |
| EX6   |               |     | 1   |

The lubricating oil compositions in Table 8 are evaluated using Pressure Differential Scanning Calorimetry (PDSC), Micro Coking Test (MCT), and Komatsu Hot Tube (KHT) oxidation bench tests. The results obtained for each lubricant are shown in Table 10.

TABLE 10

| Example | KHT 280° C. | L-85-99 OIT min | MCT |
|---------|-------------|-----------------|------|
| Comp2   | 2           | 116             | 7.23 |
| EX5     | 3           | 152             | 8.26 |
| EX6     | 3           | 140             | 7.36 |

The results show that the lubricating compositions comprising the disclosed thioether-phenols provided improved antioxidation performance while reducing deposit formation compared to the comparative formulation (Comp2) comprising the commercial phenolic antioxidant, Irganox L-135.

It is known that some of the materials described above may interact in the final formulation, so that the components of the final formulation may be different from those that are initially added. For instance, metal ions (of, e.g., a detergent) can migrate to other acidic or anionic sites of other molecules. The products formed thereby, including the products formed upon employing the composition of the present invention in its intended use, may not be susceptible of easy description. Nevertheless, all such modifications and reaction products are included within the scope of the present invention; the present invention encompasses the composition prepared by admixing the components described above.

While certain representative embodiments and details have been shown for the purpose of illustrating the subject invention, it will be apparent to those skilled in this art that various changes and modifications can be made therein without departing from the scope of the subject invention. In this regard, the scope of the invention is to be limited only by the following claims.

The invention claimed is:

1. A method of reducing deposit formation and/or corrosion in an internal combustion engine comprising contacting the internal combustion engine with a lubricating composition comprising:
   a. an oil of lubricating viscosity; and
   b. a thioether-substituted phenol ("thioether-phenol") that has the structure:

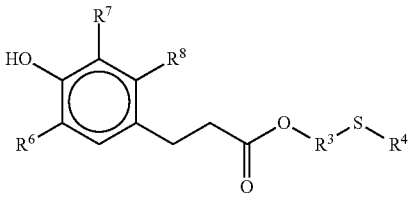

wherein $R^3$ is a $C_1$-$C_{20}$ hydrocarbyl group; $R^4$ is a $C_1$-$C_{32}$ hydrocarbyl group.

2. The method of claim 1, wherein $R^4$ is a $C_1$-$C_{18}$ hydrocarbyl group.

3. The method of claim 1, wherein said thioether-phenol comprises at least one of 2-(butylthio)ethyl 3-(3,5-di-tert-butyl-4-hydroxyphenyl)propanoate, 2-(butylthio)propyl 3-(3,5-di-tert-butyl-4-hydroxyphenyl)propanoate, 2-(butylthio)butyl 3-(3, 5-di-tert-butyl-4-hydroxyphenyl)propanoate, 2-(hexylthio)ethyl 3-(3, 5-di-tert-butyl-4-hydroxyphenyl)propanoate, 2-(hexylthio)propyl 3-(3,5-di-tert-butyl-4-hydroxyphenyl)propanoate, 2-(hexylthio)butyl 3-(3,5-di-tert-butyl-4-hydroxyphenyl)propanoate, 2-(octylthio)ethyl 3-(3,5-di-tert-butyl-4-hydroxyphenyl)propanoate, 2-(octylthio)propyl 3-(3,5-di-tert-butyl-4-hydroxyphenyl)propanoate, 2-(octylthio)butyl 3-(3,5-di-tert-butyl-4-hydroxyphenyl)propanoate, 2-(decylthio)ethyl 3-(3,5-di-tert-butyl-4-hydroxyphenyl)propanoate, 2-(decylthio)propyl 3-(3,5-di-tert-butyl-4-hydroxyphenyl)propanoate, 2-(decylthio)butyl 3-(3,5-di-tert-butyl-4-hydroxyphenyl)propanoate, 2-(dodecylthio)ethyl 3-(3,5-di-tert-butyl-4-hydroxyphenyl)propanoate, 2-(dodecylthio)propyl 3-(3,5-di-tert-butyl-4-hydroxyphenyl)propanoate, or 2-(dodecylthio)butyl 3-(3,5-di-tert-butyl-4-hydroxyphenyl)propanoate, or mixtures thereof.

4. The method of claim 1, wherein the lubricating composition further comprises at least one nitrogen-containing dispersant.

5. The method of claim 1, wherein the lubricating composition further comprises at least one overbased detergent.

6. The method of claim 1, wherein the lubricating composition comprises from 0.01 wt % to 5 wt % of said thioether-phenol based on a total weight of said lubricating composition.

\* \* \* \* \*